(12) United States Patent
Grummt et al.

(10) Patent No.: US 6,300,126 B1
(45) Date of Patent: Oct. 9, 2001

(54) EXPRESSION VECTOR FOR THE PERMANENT EXPRESSION OF FOREIGN DNA

(75) Inventors: Ingrid Grummt, Heidelberg; Friedrich Grummt, Würzburg, both of (DE)

(73) Assignee: Deutsches Krebsforschungszentrom, Heidelberg (DE)

( * ) Notice: Subject to any disclaimer, the term of this patent is extended or adjusted under 35 U.S.C. 154(b) by 0 days.

(21) Appl. No.: 09/367,927
(22) PCT Filed: Feb. 24, 1998
(86) PCT No.: PCT/DE98/00539
  § 371 Date: Aug. 20, 1999
  § 102(e) Date: Aug. 20, 1999
(87) PCT Pub. No.: WO98/37209
  PCT Pub. Date: Aug. 27, 1998

(30) Foreign Application Priority Data

Feb. 24, 1997 (DE) .............................................. 197 07 273

(51) Int. Cl.⁷ ............................. C12N 15/63; C07H 21/04
(52) U.S. Cl. ..................... 435/320.1; 435/455; 536/23.1; 536/24.1
(58) Field of Search ................................ 435/320.1, 69.1, 435/455; 536/23.1, 24.1

*Primary Examiner*—Robert A. Schwartzman
*Assistant Examiner*—Katharine F. Davis
(74) *Attorney, Agent, or Firm*—Howrey, Simon, Arnold, & White, LLP; Albert P. Halluin; Viola T. Kung

(57) ABSTRACT

The present invention relates to an expression vector having a foreign DNA. Said DNA at its 3' end has a sequence which prevents the replication of the expression vector from occurring in the opposite direction to the transcription thereof. The invention also relates to a preparation containing such an expression vector and to the use of both in the permanent expression of foreign DNA in cells.

11 Claims, No Drawings

SEQUENCE LISTING

<160> NUMBER OF SEQ ID NOS: 1

<210> SEQ ID NO 1
<211> LENGTH: 113
<212> TYPE: DNA
<213> ORGANISM: Homo sapiens

<400> SEQUENCE: 1
aggtcgacca gatgtccgaa agtgtccccc ccccccccc ccccggcgc ggagcggcgg      60 ggccactctg gactctggac tcttttttttt tttttttttt tttttttaa att          113

EXPRESSION VECTOR FOR THE PERMANENT EXPRESSION OF FOREIGN DNA

The present invention relates to an expression vector for the permanent expression of a foreign DNA. The invention also relates to a preparation containing such an expression vector and to the use of both in the permanent expression of foreign DNA in cells.

For carrying out a gene therapy it is important to introduce a foreign DNA into cells and express it therein. The former step is achieved by known methods. However, the expression of a foreign DNA in cells is often a problem, particularly when a permanent expression of the foreign DNA shall be achieved.

Therefore, it is the object of the present invention to provide a product by which a foreign DNA can permanently be expressed in cells.

According to the invention this is achieved by the subject matters defined in the claims.

Therefore, the subject matter of the present invention relates to an expression vector having a foreign DNA, a sequence being present at the 3' end of the foreign DNA which prevents the replication of the expression vector from occurring in the opposite direction to its transcription.

The present invention is based on the applicant+s finding that in eukaryotic ribosomal RNA genes, i.e. genes which are transcribed and replicated in the S phase, a sequence referred to as replication fork barrier (RGB) is present at the 3' end, which in cooperation with the transcription termination factor TTF-1 present in cells prevents the replication of the genes from occurring in the opposite direction to the transcription thereof. This serves for achieving that the DNA replication apparatus does not collide with the transcription mechanism, so that the gene expression is not discontinued.

This finding is used in the present invention for providing an expression vector having a foreign DNA, where at the 3' end of the foreign DNA a sequence is present which prevents the replication of the expression vector from occurring in the opposite direction to the transcription thereof.

The term "expression vector" comprises any vector suitable for the expression of a foreign DNA. Examples of such expression vectors are viral vectors, such as adenovirus, vaccinia virus, baculovirus and adeno-associated virus vectors. In this connection, the expression "virus vector" is understood to mean both a DNA and a viral particle. Further examples of expression vectors comprise plasmid vectors, such as pKCR, pEFBOS, cDM8 and pCEV4. In addition, artificial chromosome vectors have to be mentioned as expression vectors. They favorably contain a centromere and telomeres located at both ends of the chromosome vector as well as a replication origin. Artificial chromosome vectors are preferred according to the invention.

The expression "sequence which prevents the replication of the expression vector from occurring in the opposite direction to the transcription thereof" comprises a sequence of any kind and origin which can do so. The sequence is referred to as (RGB) below. It is favorable for (RGB) to originate from the 3' end of a gene which is both transcribed and replicated in the S phase. Examples of such a gene are eukaryotic ribosomal RNA genes from human beings, animals and plants. It is particularly favorable for (RGB) of such a gene to represent a sequence referred to as Sal Box 2 with its flanking GC region. It is most favorable for (RGB) to represent an Sal Box 2 with its flanking GC and T regions. An example of (RGB) used according to the invention is shown below. It can also have a sequence differing by one or several bases. The same applies to an (RGE) which only represents itself in the form of an Sal Box 2 with its flanking GC region. Moreover, it can be advantageous if several equal or different (RGBs) are present in an expression vector.

Example of an (RGB) used according to the invention (SEQ ID NO:1):

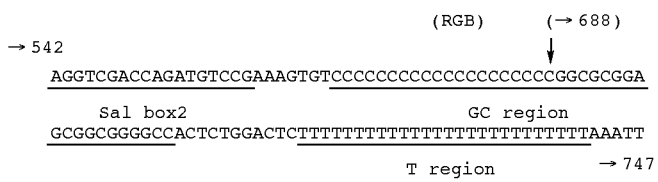

The expression "foreign DNA" comprises any DNA which can be integrated into an above expression vector. The foreign DNA can code for a diagnostically and/or therapeutically usable polypeptide. Examples of a therapeutically usable polypeptide are tumor necrosis factor, lymphokines, growth factors, plasma proteins, receptors and polypeptides increasing the immunogenicity of cells, particularly tumor cells. The latter are e.g. polypeptides which lack tumor cells, such as MHC-I polypeptides, co-stimulatory molecules, e.g. B7 polypeptides, such as B7.1 and B7.2, secretory immunostimulators, e.g. cytokines, such as IL-2, interferons and GM-CSF, and tumor-associated antigens, e.g. MAGE-1, tyrosinases or viral proteins such as E7 polypeptide of human papilloma virus and EBNA-3 polypeptide of Epstein-Barr virus. It can be advantageous for the expression of the foreign DNA to be controlled by a constitutive or inducible promoter, such as a tissue-specific or tumor-specific promoter.

An expression vector according to the invention is suitable to introduce foreign DNA into cells and express them permanently therein. The cells may be of any kind and origin. Furthermore, the cells may be present separately or in an aggregation, such as a tissue or organ. The cells can also be present inside or outside an organism. In the latter case, the cells can be kept in culture. Moreover, the cells may be healthy cells, diseased cells such as virus-infected cells or cells affected by microorganisms and protozoa, respectively, or tumor cells.

The expression vector can be introduced into cells by common methods. If the expression vector is present as viral particle, the cells can be infected therewith. However, if it is present as DNA, it can be introduced into the cells by transfection, lipofection or electroporation, for example.

A further subject matter of the present invention relates to a preparation which comprises an above expression vector and common auxiliary agents, such as buffers, diluents, carrier media, etc. In addition, the preparation can contain substances which support the effect of the polypeptide encoded by the foreign DNA of the expression vector. For example, if the expression vector contains a foreign DNA which codes for a polypeptide increasing the immunogenicity of cells, it will be advantageous for the preparation to comprise further substances increasing the immunogenicity of cells, particularly tumor-specific antigens. These antigens may be present e.g. in the form of peptides, particularly synthetic peptides. The antigens can also be present in the form of expression vectors encoding them, which can also code for HLA molecules. It is particularly favorable for the preparation to also contain the cells transduced by the expression vector and/or the nuclear blood cells stimulated by these cells. The above statements apply to the cells. In particular, it is favorable for the cells to be inactivated.

By means of the present invention it is possible to express foreign DNA permanently in cells. These cells may be located inside or outside an organism. Thus, the present invention is suited for the in vivo and ex vivo diagnosis and treatment of the most severe diseases, which are particularly tumoral diseases. The present invention represents a breakthrough in the field of gene therapy.

The invention is explained by the below example.

EXAMPLE

Production of an Expression Vector According to the Invention and its Use for the Permanent Expression of a Foreign DNA For the production of an expression vector according to the invention, an adeno-associated virus vector (AAV vector) is used which contains 5'-ITR and 3'-ITR sequences of AAV but not sequences coding for AAV-Rep and AAV-Cap proteins. Such an AAV vector is generally available. It is referred to below as pAAV. An expression cassette is inserted in pAAV between the 5'-ITR and 3'-ITR sequences of AAV. It comprises the following in the 5'- 3' direction: a mouse metallothionein promoter, a cDNA coding for human adenosine deaminase (ADA) (foreign DNA), SV40 poly A sequences, and an (RGB), as described above. For the insertion of said elements, common DNA recombination methods are carried out, the individual elements being connected with one another via a blunt-end ligation each. The resulting expression cassette is also connected with PAAV via blunt-end ligation. The pAAV-ADA expression vector according to the invention is obtained.

For its replication, pAAV-ADA is transfected together with a second expression vector, which contains an SV40 replication origin and sequences coding for AAV-Rep and AAV-Cap proteins, into cells which express an SV40-T antigen. Such cells are e.g. COS cells. The SV40 replication origin of the latter expression vector is activated by the T antigen and it is replicated. A high expression of the AAV-Rep and AAV-Cap proteins is obtained by this. pAAV-ADA is obtained as viral particle by infection of the transfected COS cells with a helper virus, e.g. adenovirus.

Such a viral particle is used for the infection of cells. The expression of the foreign DNA (ADA) is identified therein by an antibody directed against ADA. It shows that the expression of ADA is permanent.

---

---

What is claimed is:

1. An expression vector comprising a foreign DNA, wherein a sequence is present at the 3' end of the foreign DNA, which prevents the replication of the expression vector from occurring in the opposite direction to its transcription, wherein the sequence is a replication fork barrier which originates from genes which are transcribed and replicated in the S phase.

2. The expression vector according to claim 1, wherein the genes are eukaryotic ribosomal RNA genes.

3. The expression vector according to claim 1, wherein the foreign DNA is controlled by a constitutive or inducible promoter.

4. The expression vector according to claim 1, wherein the foreign DNA codes for a diagnostically and/or therapeutically usable polypeptide.

5. The expression vector according to claim 1, wherein the expression vector is a virus, plasmid or artificial chromosome vector.

6. A preparation containing the expression vector according to claim 1, and conventional auxiliary agents selected from the group consisting of buffers, diluents carrier media.

7. A method of expressing foreign DNA in cells comprising:
   (a) introducing the expression vector of claim 1 comprising the foreign DNA into the cells; and
   (b) allowing the foreign DNA to be expressed in the cells.

8. The expression vector according to claim 2, wherein the sequence comprises a Sal Box 2 with flanking GC region.

9. The expression vector according to claim 2, wherein the sequence comprises a Sal Box 2 with flanking GC and T regions.

10. The expression vector according to claim 3, wherein the promoter is a tissue-specific and/or tumor-specific promoter.

11. The preparation according to claim 6, wherein the expression vector is present in cells.

* * * * *